United States Patent [19]

Rowe et al.

[11] Patent Number: 4,584,057
[45] Date of Patent: Apr. 22, 1986

[54] MEMBRANE PROCESSES FOR SEPARATION OF ORGANIC ACIDS FROM KRAFT BLACK LIQUORS

[75] Inventors: John W. Rowe, Madison, Wis.; Harry P. Gregor, New York, N.Y.

[73] Assignee: The United States of America as represented by the Secretary of Agriculture, Washington, D.C.

[21] Appl. No.: 725,720

[22] Filed: Apr. 22, 1985

[51] Int. Cl.$^4$ ............................................. D21C 21/04
[52] U.S. Cl. ................................. 162/16; 162/30.11; 562/513; 210/638; 210/639; 210/650; 210/652; 210/724; 210/769; 204/182.1; 204/182.4
[58] Field of Search ............... 162/16, 30.11; 562/513; 210/638, 639, 650, 652, 724, 769; 204/182.1, 182.4

[56] References Cited

U.S. PATENT DOCUMENTS

| | | |
|---|---|---|
| 1,271,591 | 7/1918 | Loomis . |
| 1,723,800 | 8/1929 | Michael et al. . |
| 1,859,888 | 5/1932 | Richter . |
| 2,701,255 | 2/1955 | Heratige et al. .................. 260/435 |
| 2,926,114 | 2/1960 | Gardgaard et al. ................ 162/16 |
| 2,976,273 | 3/1961 | Ball et al. ............................ 162/16 |
| 3,136,710 | 6/1964 | Dubey ............................... 204/182.4 |
| 3,704,218 | 11/1972 | Kato et al. ....................... 204/182.4 |
| 4,470,876 | 9/1984 | Beaupré et al. ..................... 162/16 |
| 4,482,459 | 11/1984 | Shiver ................................ 210/652 |

FOREIGN PATENT DOCUMENTS

| | | | |
|---|---|---|---|
| 2711072 | 9/1977 | Fed. Rep. of Germany ...... 210/928 |
| 2926520 | 1/1980 | Fed. Rep. of Germany ........ 162/16 |
| 26367 | 2/1977 | Japan ................................. 210/928 |

OTHER PUBLICATIONS

Collins, et al., "Spent Sulfite Liquor Reducing Sugar Purification by Ultrafiltration with Dynamic Membranes", *TAPPI*, Jun. 1973, vol. 56, No. 6.

Primary Examiner—S. Leon Bashore
Assistant Examiner—Andrew J. Anderson
Attorney, Agent, or Firm—M. Howard Silverstein; David G. McConnell

[57] ABSTRACT

An aliphatic organic acid fraction is separated from the kraft black liquor by subjecting the liquor to ultrafiltration, treating the resulting permeate by electrodialysis, acidifying the resultant deionate to about pH 4–5, separating the lignin solids which precipitate following this acidification, raising the pH of the separated solution to about 7–8 and finally subjecting the neutralized solution to electrodialytic water-splitting.

7 Claims, 1 Drawing Figure

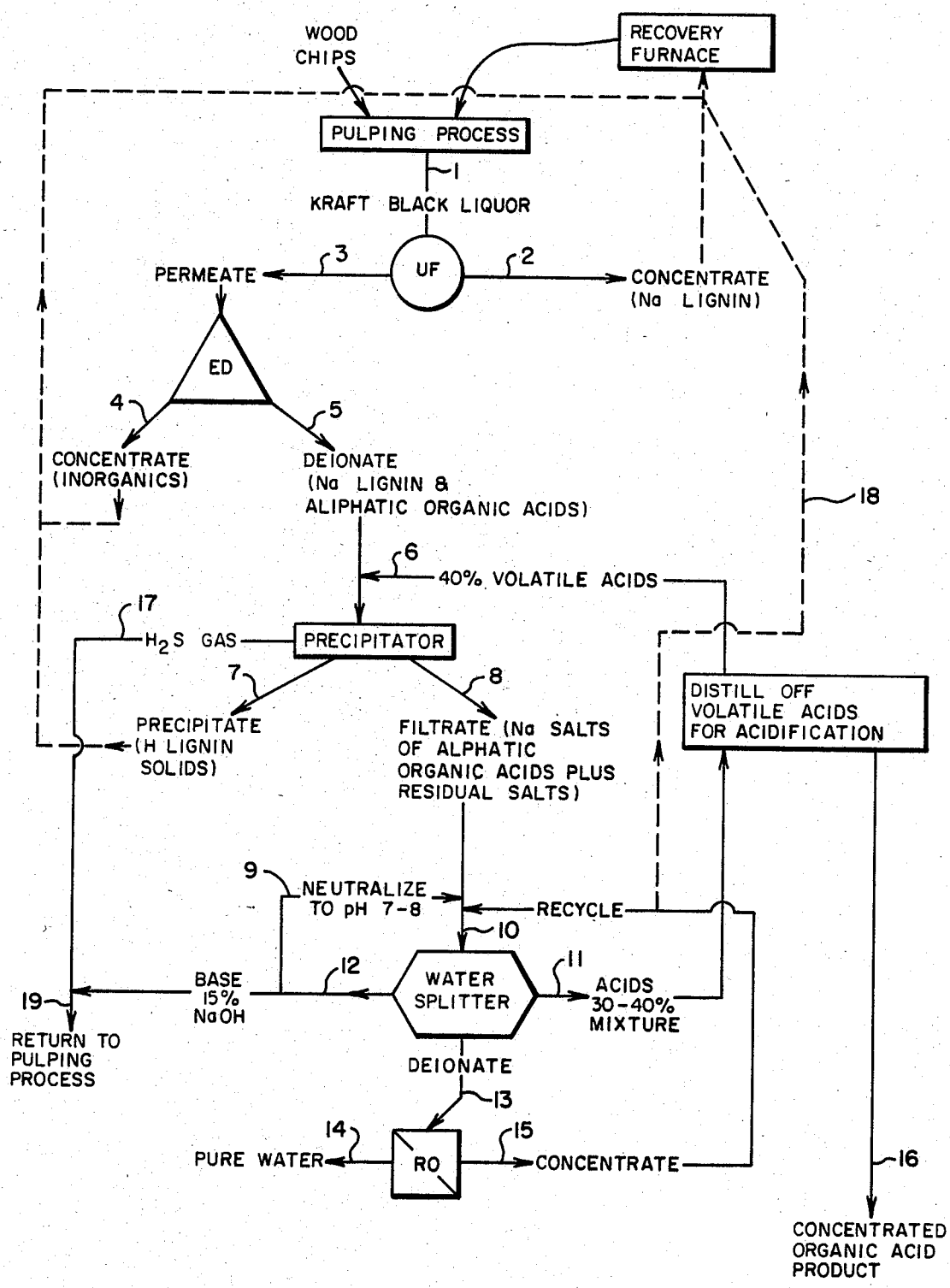

MEMBRANE PROCESSES FOR SEPARATION OF ORGANIC ACIDS FROM KRAFT BLACK LIQUORS

FIELD OF THE INVENTION

This invention relates to membrane processes for separation of organic acids from Kraft black liquors. More particularly, this invention relates to a process for the recovery of a low molecular weight, aliphatic organic acid fraction from a kraft black liquor by a series of steps including electrodialysis and electrodialytic water-splitting.

BACKGROUND OF THE INVENTION

The conventional wood pulping processes widely used in the pulp and paper industry produce very large quantities of a waste material known as kraft black liquor. Direct discharge of the kraft black liquor into the environment outside the pulp and paper plant is not commercially practicable, because it would cause very severe pollution problems. Furthermore, the kraft black liquor contains useful pulping chemicals and is also a potential source of process heat needed in the wood pulping process. Accordingly, it is conventional practice in the pulp and paper industry to concentrate the kraft black liquor and then to burn the resultant concentrate, with recovery of useful heat and concurrent recovery of valuable pulping chemicals. Although this concentration/burning process is greatly preferable to direct discharge of the kraft black liquor into the environment, it does have the disadvantage that the kraft black liquor contains a substantial amount of low molecular weight organic acids and their derivatives which have a low heat value when burned but which, if they could be separated from the black liquor, would have substantially greater value for other purposes, for example as fermentation feedstocks and chemical intermediates. While many studies of separation and purification of the various constituents of kraft black liquor have hitherto been carried out in an attempt to recover useful lignin from the liquor, relatively little attention has been directed to processes capable of economically recovering in a reasonably pure and concentrated form the organic acid constituents of the black liquor.

U.S. Pat. No. 1,271,591 issued July 9, 1918 to Loomis describes the formation of a number of fatty acids from wood and plant material by heating or by dissolution and extraction of resinous and gummy materials with fatty acids. This process is totally inapplicable to kraft black liquor.

U.S. Pat. No. 1,723,880 issued Aug. 6, 1929 to Michael et al. describes a process for preparing ammonium salts of organic acids from sulphite cellulose waste liquors by a process in which the waste liquor is heated at high pressure and the carbonaceous material produced separated, thereby producing a solution containing the ammonium salts of the organic acids produced by decomposition of the lignin in the wood. If desired, the calcium salts of these organic acids can be produced by adding calcium carbonate to the treated liquor. Again, the process is inapplicable to the treatment of kraft black liquor.

U.S. Pat. No. 1,859,888, issued May 24, 1932 to Richter describes a process for the regeneration of spent alkaline liquor resulting from the digestion of cellulosic material. In the regeneration process, the spent liquor is treated with sulphuric acid, which reacts with the sodium salts of organic acids present in the spent liquor, forming sodium sulphate and resulting in the coagulation of organic matter which can thus be separated from the remainder of the spent liquor. However, the process does not result in the separation of a low molecular weight aliphatic organic acid fraction in a reasonably pure form.

U.S. Pat. No. 2,701,255 issued Feb. 1, 1955 to Heritage et al. describes a complicated multi-stage process for separating organic products from lignocellulose. The first step of the multi-stage process is acidification to approximately pH 1.5, followed by filtration to remove the lignin precipitated by the acidification. The later stages of the process involve treatment of the delignified solution with alkaline earth metal compounds, lead compounds and alkali metal carbonates, followed by steam distillation to produce a volatile organic acid fraction. The process is not intended for treatment of kraft black liquor, and in view of its complexity it seems doubtful whether it is capable of being economically operated to produce a volatile organic acid fraction.

Finally, U.S. Pat. No. 2,926,114 issued Feb. 3, 1960 to Grangaard et al., describes a process for producing wood pulp and an organic fraction from wood by treating wood fragments in an aqueous solution of pH 7-9 at a temperature of 120-160° C. under strongly oxygenating conditions. Again, the process is not intended for the treatment of kraft black liquor.

Accordingly, it will be seen that there is a need for a process which can economically recover the low molecular weight aliphatic acids present in kraft black liquor in a reasonably pure form, while still leaving the remaining components of the liquor available for the usual combustion process, and this invention seeks to provide such a process.

SUMMARY OF THE INVENTION

This invention provides a process for the recovery of a low molecular weight, aliphatic organic acid fraction from a kraft black liquor. In the instant process, the black liquor is first subjected to ultrafiltration, thereby separating the black liquor into a concentrate enriched in the high molecular weight fraction of lignin and the permeate. The permeate produced in this first step is then subjected to electrodialysis, thus separating the permeate into a concentrate containing at least part of the inorganic acid components of the permeate and a deionate containing sodium lignin and alliphatic organic acids. Following this second, electrodialysis step, acid is added to the deionate to reduce its pH to about 4-5, thus precipitating lignin solids from the deionate and leaving a solution containing organic acids and other materials. In a fourth step of the instant process, the precipitate resulting from the third, acidification step is separated from the solution and then, in a fifth step of the instant process, the pH of this solution is raised to about 7-8. In the final, sixth step of the instant process, the solution resulting from the fifth step is subjected to electrodialytic water-splitting, thereby producing the low molecular weight, aliphatic acid organic fraction and an alkaline fraction.

BRIEF DESCRIPTION OF THE DRAWING

The accompanying drawing is a flow chart of the presently preferred process of the invention.

DETAILED DESCRIPTION OF THE INVENTION

The raw material for the instant process is kraft black liquor. Kraft black liquor is, as already mentioned, a by-product of the wood pulping processes frequently used in the pulp and paper industry. The liquor is a black, odoriferous, highly complex solution of sodium salts, sulfur compounds, lignin and the decomposition products resulting from the breakdown of carbohydrates in wood. The primary purpose of the wood pulping process is to dissolve the lignin, which acts as a glue for the wood fibers, thereby freeing the cellulose fibers for use in the production of paper. During the pulping process, considerable degradation of some of the carbohydrates to organic acids occurs, thereby producing the organic acid fraction of the kraft black liquor. The liquor is produced at an elevated temperature of about 170° C. and its composition varies widely depending upon the precise conditions of the pulping process and the nature of the wood.

In the first step of the instant process, the kraft black liquor is subjected to ultrafiltration. This ultrafiltration is very desirably performed under anaerobic conditions and the membrane used for the ultrafiltration must of course be capable of withstanding the highly alkaline kraft black liquor, and, if the ultrafiltration step is performed while the black liquor is still hot, the high temperature of the black liquor. This ultrafiltration step separates the black liquor into a concentrate containing high molecular weight sodium lignin; this concentrate can then be fed to a conventional black liquor combustion furnace and burned to recover heat which can be reused in the wood pulping process, and to recover pulping chemicals which can be recycled. The instant process has the advantage that the dewatering of the black liquor which occurs during the first ultrafiltration step effects a considerable concentration of the high molecular weight sodium lignin so that relatively little water is passed to the furnace with the sodium lignin, thereby resulting in a greater usable amount of heat being generated from the sodium lignin.

The permeate from the ultrafiltration step will typically contain low molecular weight sodium lignin, inorganic salts and sodium salts of aliphatic acids such as formic, acetic, lactic, glycolic, hydroxybutyric and other hydroxy-acids including the saccharinic acids. It is the organic acids capable of being formed from these sodium salts which are the desired products of the instant process. In the instant process, preferably the ultrafiltration step is carried out until about 90% dewatering of the high molecular weight sodium lignin occurs.

The permeate from the first, ultrafiltration step of the instant process forms the feed for the second, electrodialysis step of the process. The electrodialysis step concentrates the lower molecular weight components of the permeate, largely inorganic sodium salts, thereby enabling these concentrated inorganic components resulting from the electrodialysis step to be recycled to the furnace without returning excessive amounts of water to the furnace. The deionate from the electrodialysis step contains the sodium salts of the low molecular weight fractions of lignin and the organic acids from the black liquor. The degree of electrodialysis which can be effected in the instant process depends upon several factors, including the amount of ash present in the black liquor, the nature of this ash, and also the extent to which loss of organic ions, mainly formate and acetate, to the concentrate is allowable. Either tight or loose electrodialysis membranes of the anion-permeable type can be employed in the electrodialysis step. Electrodialysis is a process wherein a substantial number, usually 200-400 pairs, of alternating membranes in series are employed, with one membrane type being porous and containing fixed negative sulfonic acid groups which make it selectively permeable to cations, with the other membrane type also being porous and containing fixed positive quaternary ammonium groups which make it selectively permeable to anions. The usual pore sizes of these membranes allow the passage of ions up to molecular weight 250, approximately, with an increased resistance to aromatic ions because of their rigidity and greater diameter. In use, the feed solution from which ionic species are to be removed and which then constitutes the deionate, is circulated through one set of ports at opposite corners of spacers which separate the membranes and allow for the flow of solution, while the solution into which the ionic substances are concentrated circulates through a different set of ports at one other corner of each spacer, with a flow of positive current passing from left to right through the stack with the feed passing to the left of cation permeable membranes and to the right of anion permeable membranes, while the concentrate stream passes to the left of anion permeable membranes and to the right of cation permeable membranes. The positive electric current which is composed of ionic species migrating through the membrane is generated at a metallic anode at the left of the stack and a metallic cathode at its right.

Following electrodialysis, acid is added to the deionate until the pH of the deionate is reduced to about 4–5. The necessary acidification of the deionate is conveniently effected by recycling part of the organic acid fraction produced by the later electrodialytic water-splitting step of the instant process. If, as is preferred, the instant process includes a distillation step to concentrate the organic acid fraction (as described in more detail below), the acid used to acidify the deionate is preferably the concentrated organic acid fraction, which typically comprises an approximately 40% by weight solution of acetic and formic acids.

The lowering of the pH of the deionate to about 4–5 precipitates virtually all of the remaining lignin, which should then be separated from the supernatant. Separation of the precipitate can be achieved by allowing the precipitate to settle and decanting it, although if necessary centrifugation or other separation techniques may be employed to hasten the separation of the precipitate. The precipitated lignin can then be returned to the furnace.

Following the acidification and the separation of the precipitated lignin, the supernatant solution, which contains the sodium salts of the desired organic acids together with some residual inorganic salts, has its pH raised to about 7–8. Conveniently the alkali needed to effect this increase in pH of the solution is part of the alkaline fraction produced by the electrodialytic water-splitting step of the instant process.

Following the raising of the pH of the solution, the solution is submitted to electrodialytic water-splitting. During this process, the sodium ions pass through the cation-permeable membrane and form an alkaline fraction in the form of a solution of sodium hydroxide, typically in a concentration of about 15% by weight. If desired, the alkaline fraction may be recycled to the wood pulping process which originally generated the black liquor. The acid stream from the electrodialytic water-splitting reaction comprises a mixture of organic acids, typically in a concentration about 30-40% by weight. This acid stream contains relatively little of the aromatic organic acids originally present in the black liquor, the predominant acids present in the low molecular weight, aliphatic organic acid fraction from the reaction being saccharinic and related hydroxyacids, together with acetic and formic acids.

Electrodialytic water-splitting is a process wherein the stack conventionally consists of three-membrane units, such that when a positive current passes from left to right, the feed is passed into a feed compartment with an anion permeable membrane at the left and a cation permeable membrane at the right, so it is deionized by the passage of current. To the left of the anion permeable membrane is a spacer and to its left a bipolar membrane which produces hydrogen ions within it, ones which pass out to the right into the adjacent compartment to combine with anions from the feed and form acid. To the right of the cation permeable membrane is another bipolar membrane oriented in the same manner as the other bipolar membrane so it produces hydroxide anions which pass out to the left and form bases with cations leaving the feed compartment. Thus, each cell in series produces acid in the left cell, a deionate in the center cell and a base in the right-hand cell, with a stack containing 200-400 cell units, as in the case of electrodialysis.

The organic acid fraction from the electrodialytic water-splitting step can be separated by distillation to produce a concentrate of the lower molecular weight, more volatile acetic and formic acids, typically in a concentration of about 40% by weight. It is this acetic/formic acid concentrate which is preferably used for acidification in the acidification and lignin precipitation step of the instant process. Alternatively, in place of distillation, separation of the acetic and formic acids from the hydroxyacids may be achieved by an electrodialysis membrane separation employing very fine pore membranes. The residue from the distillation or ED membrane separation is of course concentrated in hydroxyacids and may be used as a source of such acids.

In addition to the alkaline and acid fractions already discussed, the electrodialytic water-splitting reaction also, of course, produces a deionate. Desirably, this deionate stream is then concentrated by reverse osmosis, the best and most economical concentration technique for this type of material. This reverse osmosis step produces a concentrate which can be recyled to the electrodialytic water-splitting step; the reverse osmosis concentration provides the water-splitting step with a feed sufficiently concentrated so that the resistance and power dissipation in the water-splitting device are low, thereby keeping the power consumption correspondingly low. The reverse osmosis step also serves to control the water content in the instant process and makes a stream of pure water available for reuse as desired.

The following example is now given, though by way of illustration only, to illustrate the presently preferred variant of the instant process. A flow diagram of this preferred process is shown in the accompanying drawing.

The accompanying drawing shows schematically a wood pulping process in which wood chips are treated with pulping chemicals from a recovery furnace; obviously, make-up amounts of pulping chemicals may need to be added, but these are omitted from the flow diagram for the sake of simplicity. Among the products of the pulping process is a stream 1 of kraft black liquor, the composition of which is shown in Table I below. Obviously, all kraft black liquors are not identical and the composition of the liquor may vary considerably depending upon the exact process and the raw material employed. Accordingly, this example will describe the preferred process as applied to a typical black liquor stream containing 82% by weight water; other black liquor streams may be more dilute or more concentrated, and the relative amounts of non-aqueous components present can vary considerably.

In Table I, the designation HL refers to high molecular weight lignin, having a molecular weight of 355 and up. High molecular weight lignin is the complex material which occurs over a wide range of molecular weights ranging from many thousands down to a few hundred. Almost all the high molecular weight lignin components are soluble as sodium salts in strongly alkaline solutions but become insoluble in slightly acid solutions at pH 4-5. The designation HIn in Table I refers to inorganic constituents (measured as inorganic acids); these include carbonate, sulfide and a number of other sulfur compounds, and the mixture has an equivalent weight of about 28. The designation HOr in Table I refers to water-soluble hydroxyacids, mainly glycolic and saccharinic acids that are formed by alkaline degradation of carbohydrates during the wood pulping process. The designation HAc in Table I refers to combined acetic and formic acid content, in which the acetic acid predominates.

Kraft black liquor normally also contains small amounts of tall oil soap, but this soap can be skimmed off prior to treatment of the kraft black liquor by the instant method and hence is not shown in the flow diagram.

The first step in the preferred process is treating the kraft black liquor stream 1 by ultrafiltration to produce a concentrate 2 concentrated in the high molecular weight sodium lignin and comprising approximately 33 percent solids, and a permeate 3 containing low molecular weight salts and approximately 16 percent in total solids. It is estimated that the division between the concentrate and the permeate occurs at approximately molecular weight 1,000 with most ultrafiltration membranes. The concentrate 2 is returned to the recovery furnace for combustion.

The permeate 3 from the ultrafiltration step is then fed to an electrodialysis cell. The preliminary ultrafiltration step removes the high molecular weight lignin constituents of the black liquor which would otherwise foul the electrodialysis cell. The optimum degree of electrodialysis depends upon the nature of the feed and the nature of the other steps in the process. In this particular case, the electrodialysis is continued until 83% of the inorganic salts pass through the electrodialysis membranes to form a concentate 4 having a total solids content of about 26%. This concentrate 4 is returned to the recovery furnace. The material which does not pass through the electrodialysis membranes forms a deionate 5 consisting primarily of the sodium salts of the various organic acids, together with a minor amount of inorganic salts, and having a relatively low total solids content of approximately 14%.

To this deionate 5 is added a mixture 6 of acetic and formic acids produced by the water-splitting and concentration steps described below. The addition of the acid mixture 6 to the deionate 5 generates hydrogen sulfide gas 17 (mixed with a minor amount of carbon dioxide), which is returned to the pulping process as indicated at 19 in the accompanying drawing, and also precipitates virtually all of the low molecular weight fractions of the lignin to produce a precipitate 7 which is separated from the accompanying filtrate 8 and returned to the recovery furnace. The filtrate 8 is composed largely of the sodium salts of the organic acids, together with some residual inorganic salts. The filtrate 8 is then treated with an alkaline stream 9 derived from the water-splitting reaction described below, thereby raising the pH of the filtrate 8 to approximately 7-8 in order to ionize all the acids present.

The acidified filtrate 10 then becomes the feed to an electrodialytic water-splitting step. In this step, the anions present in the neutralized filtrate 10 are combined with hydrogen ions from the bipolar membrane to produce a low molecular weight aliphatic organic acid fraction 11, typically having a concentration of 30-40%, the exact concentration being determined largely by the electroosmotic coefficient of the anion-permeable membrane. The electrodialytic water-splitting step also produces an alkaline fraction 12 in the form of a solution of sodium hydroxide having a concentration of about 15% by weight. A minor proportion of this alkaline fraction 12 is recycled as the alkaline stream 9 used to neutralize the filtrate 8, while a major proportion of the alkaline fraction 12 is returned directly to the pulping process, as indicated at 19 in the accompanying drawing. Finally, the water-splitting step produces a deionate stream which is relatively dilute and which is passed to a reverse osmosis cell where it is separated into a pure water stream 14 and a concentrate stream 15 having a solids content of about 6%. Part of the concentrate 15 is recycled and added to the neutralized filtrate to form the feed 10 to the electrodialytic water-splitting step. The remainder of the concentrate 15 is recylced as a stream 18 to the recovery furnace. If the anion-permeable membrane used is fairly tight, the water soluble aromatic lignin acids originally present in the kraft black liquor which are not precipitated during the acidification/precipitation step into the precipitate 7 will accumulate in the deionate 13 and hence in the concentrate 15. Returning part of the concentrate 15 to the furnace as the stream 18 disposes of these aromatic lignin acids.

The acid fraction 11 from the water-splitting step is subjected to distillation to distill off the volatile acids, thereby producing the 40% acid stream 6 which is used for acidification of the deionate 5. The distillation step also produces a concentrated organic acid product 16 as the final product of the process. If desired, a membrane separation process might be substituted for the distillation step, with consequent energy savings.

Analysis of all streams shown in the accompanying drawing is given in Table I below. From this Table, it will be seen that of the 82 parts of water originally present in 100 parts of the kraft black liquor 1, only 27 parts are recylced directly back to the recovery furnace, eight parts in the ultrafiltration concentrate 2, twelve in the electrodialysis concentrate 4 and seven parts divided between the lignin and the lignin precipitate 7 and the recycled stream 18. Thirty-six parts of pure water are recovered for reuse as the pure water stream 14 from the reverse osmosis operation, ten parts of water are present in the alkaline fraction 12 recycled to the pulping process and nine parts of water remains with the organic acid product 16. Since only 33% of the water (27 parts out of 82) originally contained in the kraft black liquor requires evaporation in the recovery furnace, the preferred variant of the instant process achieves energy savings of approximately 60 percent and also allows the recovery of valuable by-products. In addition, the preferred variant reduces the amount of sodium returned to the recovery furnace by about 50%, thereby reducing the need for lime to convert the carbonate furnace product back into hydroxide before recycle to the pulping process, thereby effecting further energy savings. Of the 18 parts of solids originally present in each 100 parts of kraft black liquor, over three parts of organic acids are recovered in a concentrated stream of about 40% acid content by weight by use of the instant process.

Thus, the instant process has three principal advantages. Firstly, it recovers the organic acids as useful by-products from the kraft black liquor. Since these organic acids have a relatively low heat content, their loss of heating value is negligible, and they are much more valuable separated for use as other purposes, for example chemical feedstocks. Secondly, the amount of fuel needed in the recovery furnace to evaporate water is greatly reduced. Thirdly, the amount of lime needed to convert the carbonate furnace product back to hydroxide for recycle to the pulping process is also greatly reduced.

It will be apparent to those skilled in the arts that numerous changes and modifications may be made in the preferred embodiments of the invention described above without departing from the scope of the invention. Accordingly, the whole of the foregoing description is to be construed in an illustrative and not in a limitative sense, the scope of the invention being defined solely by the appended claims.

TABLE I

BLACK LIQUOR STREAM COMPOSITIONS
Starting with 100 parts (by weight) of Kraft Black Liquor

| No. | Stream | Water | HL | HIn | HOr | HAc | NaOH |
|---|---|---|---|---|---|---|---|
| 1. | KBL Feed | 82 | 6.4 | 2.0 | 3.6 | 1.4 | 8.2 |
| 2. | UF Conc. | 8 | 2.4 | .2 | .4 | .1 | 1.0 |
| 3. | UF Perm. | 74 | 4.0 | 1.8 | 3.2 | 1.3 | 7.2 |
| 4. | ED Conc. | 12 | .0 | 1.5 | .3 | .6 | 3.2 |
| 5. | ED Deion. | 62 | 4.0 | .3 | 2.9 | .6 | 4.0 |
| 6. | Add HAc | 2.4 | .0 | .0 | .0 | 1.1 | .0 |
| 7. | Precipitate | 7 | 3.9 | .1 | .0 | .1 | .2 |
| 8. | Filtrate | 57 | .1 | .0 | 2.9 | 1.6 | 3.8 |
| 9. | Neutralize | 2 | .0 | .0 | .0 | .0 | .3 |
| 10. | Feed to WS | 62 | .1 | .0 | 3.0 | 1.6 | 4.4 |
| 11. | Acid from WS | 11 | .0 | .0 | 2.9 | 1.6 | .0 |
| 12. | Base from WS | 12 | .0 | .0 | .0 | .0 | 4.1 |
| 13. | WS Deion. | 39 | .1 | .0 | .1 | .0 | .3 |
| 14. | RO Perm. | 36 | .0 | .0 | .0 | .0 | .0 |
| 15. | RO Conc. | 3 | .1 | .0 | .1 | .0 | .3 |
| 16. | Org. Acids | 9 | .0 | .0 | 2.9 | .5 | .0 |
| 17. | Gas from pptn. | 0 | .0 | .2 | .0 | .0 | .0 |
| 18. | Bleed to Furnace | .3 | .1 | .0 | .0 | .0 | .0 |
| 19. | Pulping Soln. | 10 | .0 | .2 | .0 | .0 | 3.8 |

We claim:

1. A process for the recovery of a low molecular weight, aliphatic organic acid fraction from a kraft black liquor, which process comprises (a) subjecting said black liquor to ultrafiltration, thereby separating said black liquor into a concentrate enriched in the high molecular weight fraction and a permeate;

(b) subjecting the permeate produced in step (a) to electrodialysis, thereby separating the permeate into a concentrate containing at least part of the inorganic acid components of the permeate and a deionate containing sodium lignin and aliphatic organic acids;

(c) adding to the deionate produced in step (b) sufficient acid to reduce the pH thereof to about 4 to 5, thereby precipitating lignin solids from the deionate and leaving a solution containing inorganic acids and other materials;

(d) separating the precipitate formed in step (c) from the solution produced therein;

(e) raising the pH of the separated solution produced in step (d) to about 7 to about 8; and (f) subjecting the solution produced in step (e) to electrodialytic water-splitting, thereby producing a low molecular weight, aliphatic acid organic fraction and an alkaline fraction.

2. A process according to claim 1 wherein the ultrafiltration of step (a) is conducted under substantially anaerobic conditions.

3. A process according to claim 1 wherein said low molecular weight, aliphatic organic acid fraction produced in step (f) is concentrated by distillation and part of the resultant concentrated acid fraction is recycled and used as the acid added in step (c).

4. A process according to claim 1 wherein step (f) also produces a deionate fraction and said deionate fraction is subjected to reverse osmosis, thereby producing a permeate comprising purified water and a concentrate, said concentrate being recycled to step (f) of said process.

5. A process according to claim 1 wherein a part of said alkaline fraction produced in step (f) is recycled and used to effect said raising of the pH of said solution in step (e) of said process.

6. A process according to claim 1 wherein said kraft black liquor is produced in a wood pulping process and at least part of said alkaline fraction produced in step (f) is recycled to said wood pulping process.

7. A process according to claim 1 wherein said kraft black liquor is produced in a wood pulping process and wherein said acidification in step (c) results in the release of hydrogen sulfide gas, which is recycled to said wood pulping process.

* * * * *